US009669988B2

(12) United States Patent
Kojima et al.

(10) Patent No.: US 9,669,988 B2
(45) Date of Patent: Jun. 6, 2017

(54) FIXED AMOUNT DISCHARGE CONTAINER

(75) Inventors: Takashi Kojima, Soka (JP); Nobuo Yokouchi, Omitama (JP); Naoki Kato, Omitama (JP); Kenji Kaitsuka, Omitama (JP); Takeshi Iida, Omitama (JP)

(73) Assignee: Santen Pharmaceutical Co., LTD., Osaka-shi, Osaka (JP)

( * ) Notice: Subject to any disclaimer, the term of this patent is extended or adjusted under 35 U.S.C. 154(b) by 0 days.

(21) Appl. No.: 14/114,093

(22) PCT Filed: Apr. 26, 2012

(86) PCT No.: PCT/JP2012/061236
§ 371 (c)(1),
(2), (4) Date: Jan. 10, 2014

(87) PCT Pub. No.: WO2012/147862
PCT Pub. Date: Nov. 1, 2012

(65) Prior Publication Data
US 2014/0124542 A1    May 8, 2014

(30) Foreign Application Priority Data
Apr. 26, 2011  (JP) ................. 2011-098003

(51) Int. Cl.
*B65D 88/54*    (2006.01)
*B65D 83/00*    (2006.01)
(Continued)

(52) U.S. Cl.
CPC ....... *B65D 83/0033* (2013.01); *A61M 5/3129* (2013.01); *A61M 5/31501* (2013.01);
(Continued)

(58) Field of Classification Search
CPC ....... B65D 83/0033; B65B 3/32; G01F 11/06; G01F 11/04; A61M 5/3156; A61M 5/31561; A61M 5/31563; A61M 5/178
(Continued)

(56) References Cited

U.S. PATENT DOCUMENTS 963,051 A * 7/1910 Kooken .................. 604/208
2,409,656 A * 10/1946 Austin .................... 604/210
(Continued)

FOREIGN PATENT DOCUMENTS

AU    560426 B2    4/1987
CN    1282260 A    1/2001
(Continued)

OTHER PUBLICATIONS

Aug. 26, 2014—(EP) Extended Search Report—App 12776550.1.
(Continued)

*Primary Examiner* — Lien Ngo
(74) *Attorney, Agent, or Firm* — Banner & Witcoff, Ltd.

(57) ABSTRACT

A fixed amount discharge container includes: a syringe barrel 3; and a piston 8 inserted in the syringe barrel 3 so as to be movable in a longitudinal direction, thereby defining a fluid chamber between the syringe barrel 3 and the piston 8. One of the syringe barrel 3 and the piston 8 includes a guide 3c that is extended in a longitudinal direction. The other of the syringe barrel 3 and the piston 8 includes a slider 9 that is movable in the guide 3c along with the other of the syringe barrel 3 and the piston 8. The guide 3c is provided with a target position contact portion 3j which the slider 9 contacts when an amount of the fluid chamber is equal to a target amount.

5 Claims, 13 Drawing Sheets

(51) Int. Cl.
*A61M 5/31* (2006.01)
*A61M 5/315* (2006.01)

(52) U.S. Cl.
CPC ....... *A61M 5/3159* (2013.01); *A61M 5/31525* (2013.01); *A61M 5/31591* (2013.01); *A61M 2005/31508* (2013.01)

(58) Field of Classification Search
USPC ............... 222/309, 43, 49; 604/207–210
See application file for complete search history.

(56) References Cited

U.S. PATENT DOCUMENTS

| | | | | |
|---|---|---|---|---|
| 2,428,577 | A | * | 10/1947 | Mathis ..................... 222/214 |
| 2,502,639 | A | * | 4/1950 | Blake ....................... 604/210 |
| 2,648,334 | A | * | 8/1953 | Brown et al. ............. 604/205 |
| 2,695,023 | A | * | 11/1954 | Brown ....................... 604/210 |
| 4,050,459 | A | | 9/1977 | Sanchez |
| 4,117,728 | A | * | 10/1978 | Johnson .................. 73/864.18 |
| 4,154,108 | A | * | 5/1979 | Vollinger et al. ......... 73/864.13 |
| 4,261,205 | A | * | 4/1981 | Oshikubo et al. ........ 73/864.14 |
| 4,466,426 | A | * | 8/1984 | Blackman ................. 604/187 |
| 4,610,668 | A | * | 9/1986 | Fleig ......................... 604/208 |
| 4,832,694 | A | * | 5/1989 | Raphael, III ............ A61M 5/50 604/110 |
| 4,962,868 | A | | 10/1990 | Borchard ................. 222/49 |
| 5,284,132 | A | * | 2/1994 | Geier ..................... A61M 11/02 128/200.22 |
| 5,318,544 | A | * | 6/1994 | Drypen et al. ............ 604/210 |
| 6,322,542 | B1 | * | 11/2001 | Nilson et al. .............. 604/257 |
| 8,267,911 | B2 | * | 9/2012 | Gallogly ................ A61B 5/1427 604/403 |
| 8,376,993 | B2 | * | 2/2013 | Cox ..................... A61M 5/31593 604/110 |
| 8,851,339 | B2 | * | 10/2014 | Schultz et al. ............ 222/386 |
| 2005/0015055 | A1 | | 1/2005 | Yang |
| 2006/0084919 | A1 | | 4/2006 | Shaw et al. |
| 2008/0114305 | A1 | | 5/2008 | Gerondale |
| 2008/0221517 | A1 | | 9/2008 | Shaw et al. |
| 2008/0302932 | A1 | | 12/2008 | Mosler et al. |
| 2008/0306424 | A1 | | 12/2008 | Gallogly et al. |
| 2009/0326479 | A1 | * | 12/2009 | Janish et al. .................. 604/218 |
| 2010/0081999 | A1 | | 4/2010 | Rueckert et al. |
| 2011/0033224 | A1 | | 2/2011 | Schultz et al. |
| 2014/0039410 | A1 | | 2/2014 | Harms et al. |
| 2016/0310669 | A1 | | 10/2016 | Harms et al. |
| 2016/0331906 | A1 | | 11/2016 | Harms et al. |

FOREIGN PATENT DOCUMENTS

| | | | |
|---|---|---|---|
| DE | 8509572 | U1 | 8/1985 |
| FR | 711644 | * | 9/1931 ............... 604/208 |
| FR | 1156298 | A | 5/1958 |
| FR | 1412547 | A | 10/1965 |
| JP | 60-175249 | U | 11/1985 |
| JP | 08-268480 | A | 10/1996 |
| JP | 2001-299913 | A | 10/2001 |
| JP | 2001-526097 | A | 12/2001 |
| JP | 2008302195 | A | 12/2008 |
| WO | 2006/020756 | A2 | 2/2006 |

OTHER PUBLICATIONS

Aug. 21, 2015—(CN) Office Action—App 201280020440.2.
Feb. 16, 2016—(JP)—Office Action App. 2013-512434.
Dec. 4, 2015—(MX)—Office Action App. MX/a/2013/012370.
Nov. 19, 2015—(AU)—Examination Report App. 2012248256.
Dec. 1, 2015—(CN)—Office Action App. 201280020440.2.
May 11, 2016—(MX)—Office Action App. MX/a/2013/012370.
Mar. 30, 2016—(EA)—Office Action App. 201391576.
Apr. 13, 2016—(AU)—Examination Report App. 2012248256.
May 10, 2016—(CN)—Office Action App. 201280020440.2.
Aug. 23, 2016 (AU) Office Action—App. 2012248256.
International Search Report issued in corresponding International Application No. PCT/JP2012/061236 mailed Aug. 7, 2012.
Nov. 14, 2016 (CL) Office Action—App. 201303095.
Aug. 30, 2016 (JP) Office Action—App. 2013-512434.
Nov. 23, 2016—(CN)—Office Action App. 201280020440.2.
Dec. 5, 2016 (EA) Office Action—App. 201391576.
Feb. 7, 2017—(EP) Office Action—App 12776550.1.
Jan. 16, 2017—(MX)—Office Action App. MX/a/2013/012370.

* cited by examiner

FIXED AMOUNT DISCHARGE CONTAINER

CROSS REFERENCE TO RELATED APPLICATIONS

This is a U.S. National Phase Application under 35 U.S.C. §371 of International Application No. PCT/JP2012/061236 filed Apr. 26, 2012, which was published Under PCT Article 21(2), which claims priority to Japanese Application No. 2011-098003, filed Apr. 26, 2011, the entire contents of which are incorporated herein by reference.

TECHNICAL FIELD

The invention relates to a fixed amount discharge container including a piston that is slidably provided within a syringe barrel.

BACKGROUND ART

A syringe is as an example of a container that ejects a predetermined amount of fluid. The syringe is structured so as to be able to administer a given amount of medical solution required for dispensing.

The example is a syringe described in Patent Document 1. In the syringe described in Patent Document 1, a scale for measuring an amount of medical solution required for dispensing is provided on an outer periphery of a syringe barrel. Dispensing can be practiced easily, accurately by aligning a piston to the scale.

RELATED ART DOCUMENT

Patent Document

Patent Document 1: JP-A-2001-299913

SUMMARY OF INVENTION

Technical Problem

As above, in order to draw in a required amount of medical solution, the syringe described in Patent Document 1 requires accurately aligning the piston to the scale provided on the outer periphery of the syringe barrel. For this reason, a user must pay attention to the piston and the scale at all times while consciously performing visual verification. Moreover, the amount of fluid to be drawn in varies from one user to another.

Accordingly, an object of the invention is to provide a fixed amount discharge container capable of easily ejecting a predetermined amount of fluid at all times.

Solution To Problem

In light of the problem, a fixed amount discharge container according to the invention comprises:
  a syringe barrel; and
  a piston, inserted in the syringe barrel so as to be movable in a longitudinal direction, thereby defining a fluid chamber between the syringe barrel and the piston, wherein
    one of the syringe barrel and the piston includes a guide that is extended in a longitudinal direction;
    the other of the syringe barrel and the piston includes a slider that is movable in the guide along with the other of the syringe barrel and the piston; and
    the guide is provided with a target position contact portion which the slider contacts when a amount of the fluid chamber is equal to a target amount.

According to the invention, the fixed amount discharge container may be configured such that:
  the guide includes a plurality of grooves;
  the grooves that are adjacent to each other are formed such that axial lines of the grooves differ from each other; and
  the grooves that are adjacent to each other are connected at a connecting portion; and
  a wall of the connecting portion that extends in a circumferential direction is performed as the target position contact portion.

According to the invention, the fixed amount discharge container may be configured such that:
  the guide is formed in the syringe barrel as a through hole that penetrates through the syringe barrel in a radial direction; and
  the slider is removably attached to the piston from the outside the syringe barrel.

Further, according to the invention, the fixed amount discharge container may comprise an adaptor that changes the target amount.

Advantageous Effects of Invention

The fixed amount discharge container of the invention allows the user to ascertain a point in time when the amount of the fluid chamber filled with fluid has become equal to the target amount from the fact that the slider has contacted the target position contact portion. Therefore, it is possible to provided a fixed amount discharge container that can readily, accurately eject a target amount of fluid at all times.

DESCRIPTION OF EMBODIMENTS

Figure 1:
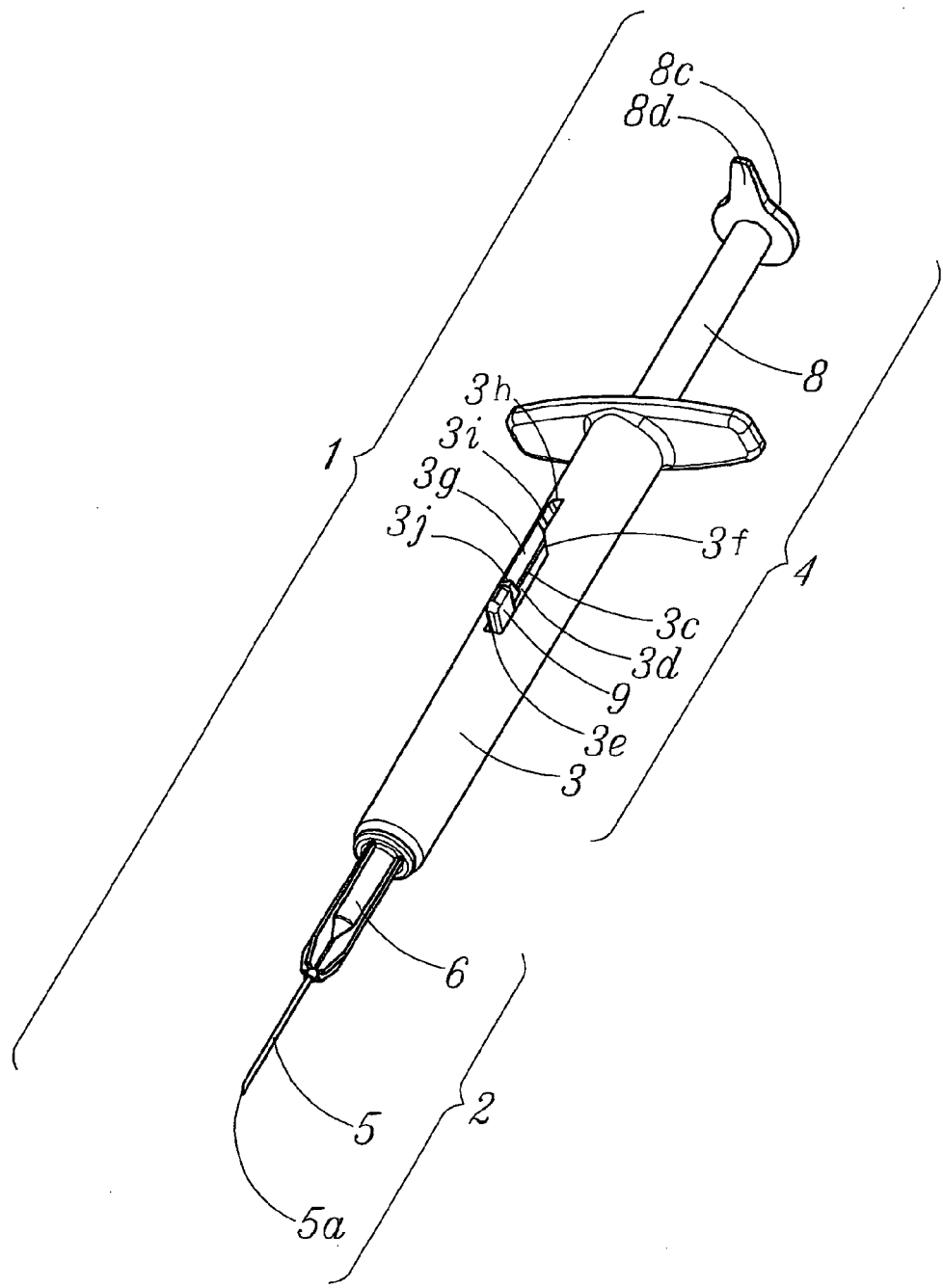
FIG. 1 is a perspective view of an entire syringe of an embodiment before a medicine is drawn and after the medicine is dispensed.
Figure 2:
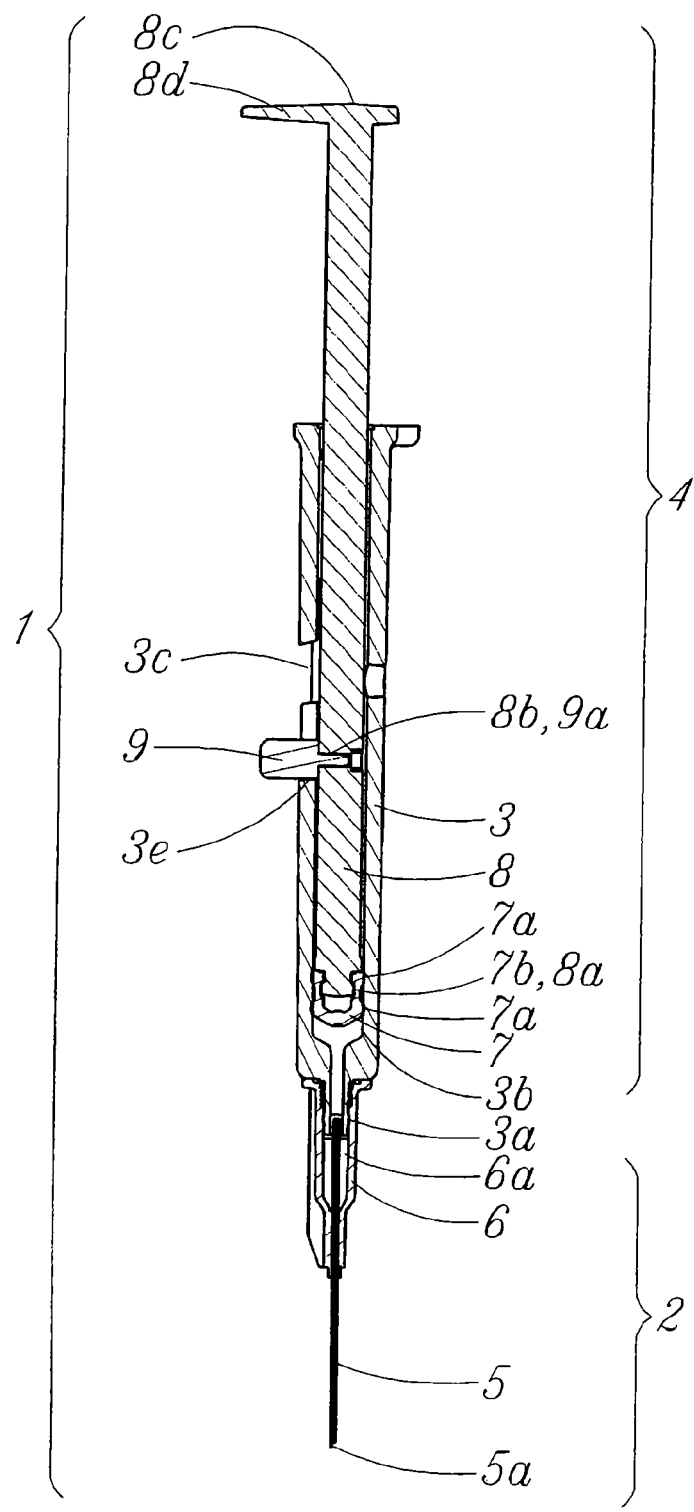
FIG. 2 is a longitudinal cutaway side view of the syringe shown in FIG. 1.
Figure 3:
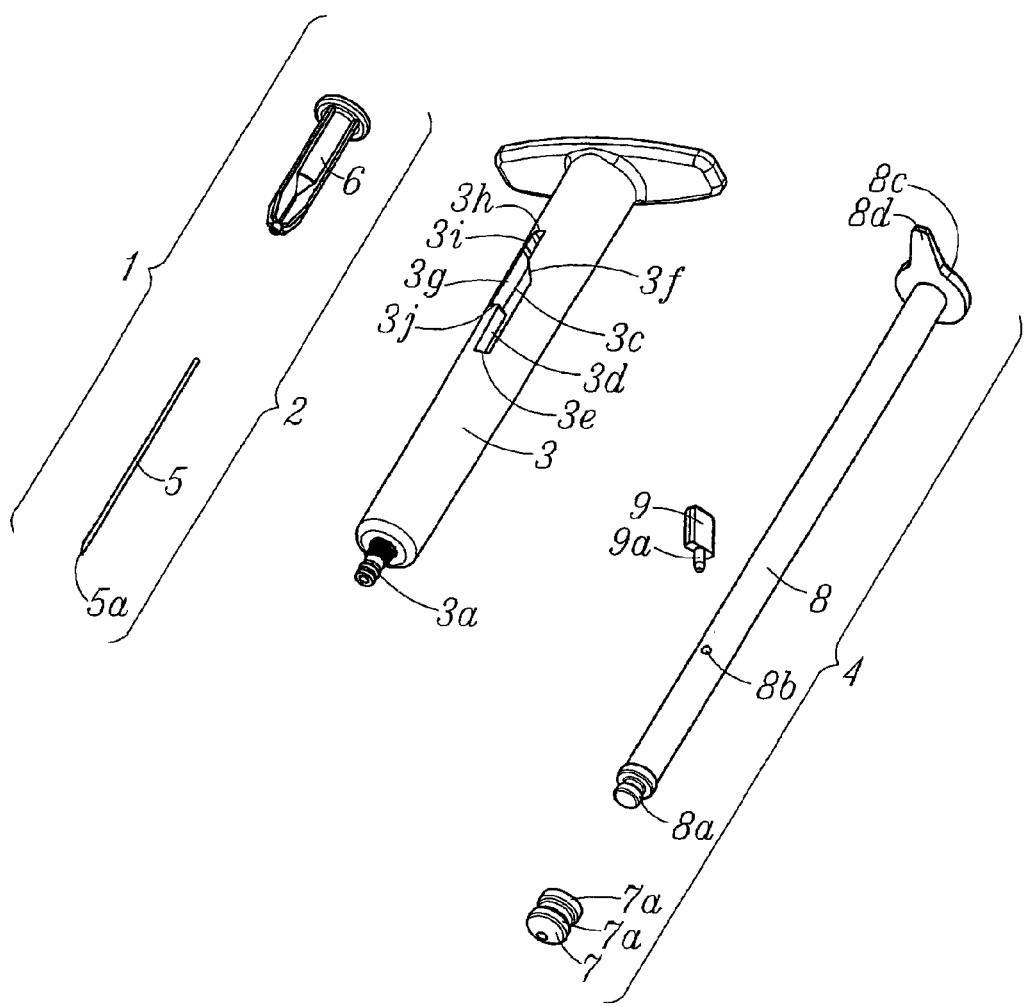
FIG. 3 is an exploded perspective view of the syringe shown in FIG. 1.

An embodiment in which a fixed amount discharge container of the invention is applied to a syringe 1 is now described by reference to FIG. 1 to FIG. 6.

The syringe 1 of the embodiment is made up of an injection needle set 2, a syringe barrel 3, and a piston set 4. The injection needle set 2 is screw-engaged with a front part of the syringe barrel 3. In the injection needle set 2, a needle 5 is fixedly press-fitted to a needle base 6. An inner diameter portion 6a of the needle base 6 and a rib 3a of the syringe barrel 3 are fixedly press-fitted together, thereby preventing a medical solution from leaking out from any other location except a tip end of the injection needle. The needle 5 is formed from stainless steel, and the needle base 6 is formed from PP (polypropylene).

The syringe barrel 3 is a substantially tubular member that extends in its longitudinal direction. The piston set 4 is inserted into an inner diameter portion 3b of the syringe barrel 3 so as to be movable in the longitudinal direction of the syringe barrel 3. A fluid chamber is defined between the syringe barrel 3 and a tip end of a gasket 7 of the piston set 4. An amount of the fluid chamber can be changed by moving the piston set 4 with respect to the syringe barrel 3.

An outer diameter projection 7a of the gasket 7 is press-fitted into the inner diameter portion 3b of the syringe barrel 3 in a slidable fashion. The gasket 7 is formed from butyl rubber, which is a soft member, and capable of compression and deformation. This prevents a medical solution from leaking out from clearance between the gasket 7 and the inner diameter portion 3b of the syringe barrel 3. In order to enhance slidability to a much greater extent, silicon is applied on an outer periphery of the gasket 7. The syringe barrel 3 is formed from PP (polypropylene).

A configuration of the piston set 4 is now described. The gasket 7 positioned in front of a piston 8 is fixed to the piston 8 such that an inner diameter concave 7b of the gasket 7 and a front end projection 8a of the piston 8 are rotatable in a circumferential direction of the syringe barrel 3.

The slider 9 is press-fitted into an insertion hole 8b of the piston 8 formed in a vertical direction with respect to the longitudinal direction of the syringe barrel 3. The piston 8 is formed from PP (polypropylene), and the slider 9 is formed from PP (polypropylene).

The slider 9 is configured to be movable with respect to the longitudinal direction of the syringe barrel 3 along a guide 3c of the syringe barrel 3 by moving the piston set 4 with respect to the syringe barrel 3. The slider 9 is configured to be movable also in a peripheral direction of the syringe barrel 3.

A method for operating the syringe 1 is now described. Operation of the syringe 1 includes three operations; namely, suction, bubble removal, and dispensing.

In a state of the syringe 1 achieved before being used; namely, a state acquired before the syringe 1 draws in a medical solution from a vial by suction, the slider 9 remains in contact with a front end 3e of a first groove 3d as illustrated in FIG. 1. In short, the piston set 4 is situated at the foremost end.

Figure 4:
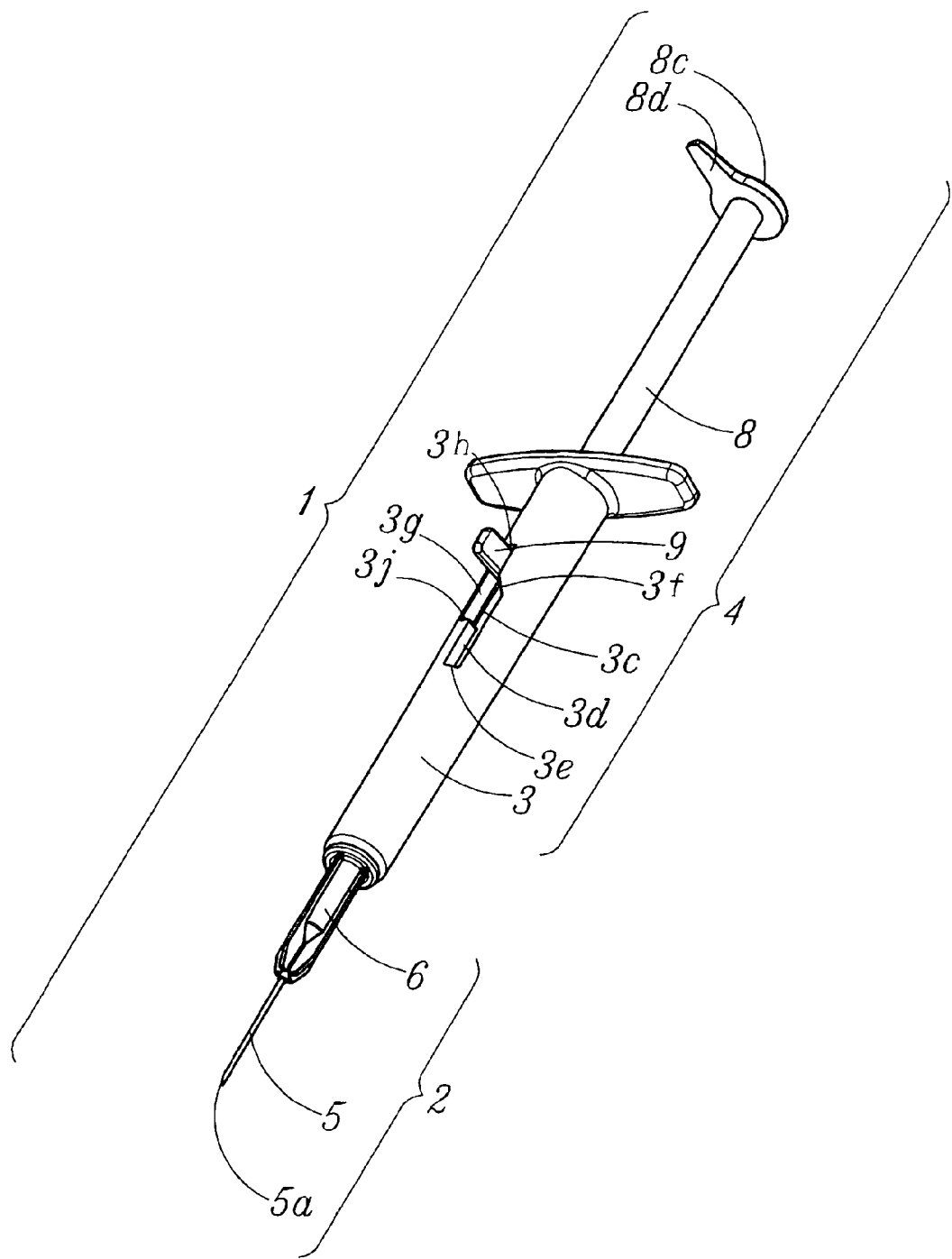
FIG. 4 is a perspective view of the entire syringe that is shown in FIG. 1 and acquired after it finishes drawing in a medicine.

Next, the piston set 4 is pulled backward with respect to the syringe barrel 3 in order to draw in the medical solution from the vial, whereupon the slider 9 comes into contact with a slope 3f. The slider 9 then moves to a second groove 3g while turning along the slope 3f. When the piston set 4 is continuously pulled backward furthermore, the slider 9 contacts a rear end face 3h of the second groove 3g as illustrated in FIG. 4, whereupon the piston set 4 is situated at a rearmost end of the movable range. The slider 9 is at this time fixed to a guide member 3c by means of a rib 3i projecting toward an interior of the guide 3c while the slider 9 remains in a slightly press-fitted state. After completion of suction in this state, an interior of the fluid chamber becomes filled with the medical solution.

Since the slider 9 remains in contact with a rear end face 3h of the guide 3c, the piston set 4 will not move backward any further. Specifically, there is no fear that the piston set 4 might get out of the syringe barrel 3 in a backward direction.

In addition, so long as the injection needle set 2 is removed in this state and provided with a cap instead, sterilized, and packaged, the syringe can also be utilized as a pre-filled syringe.

Figure 5:
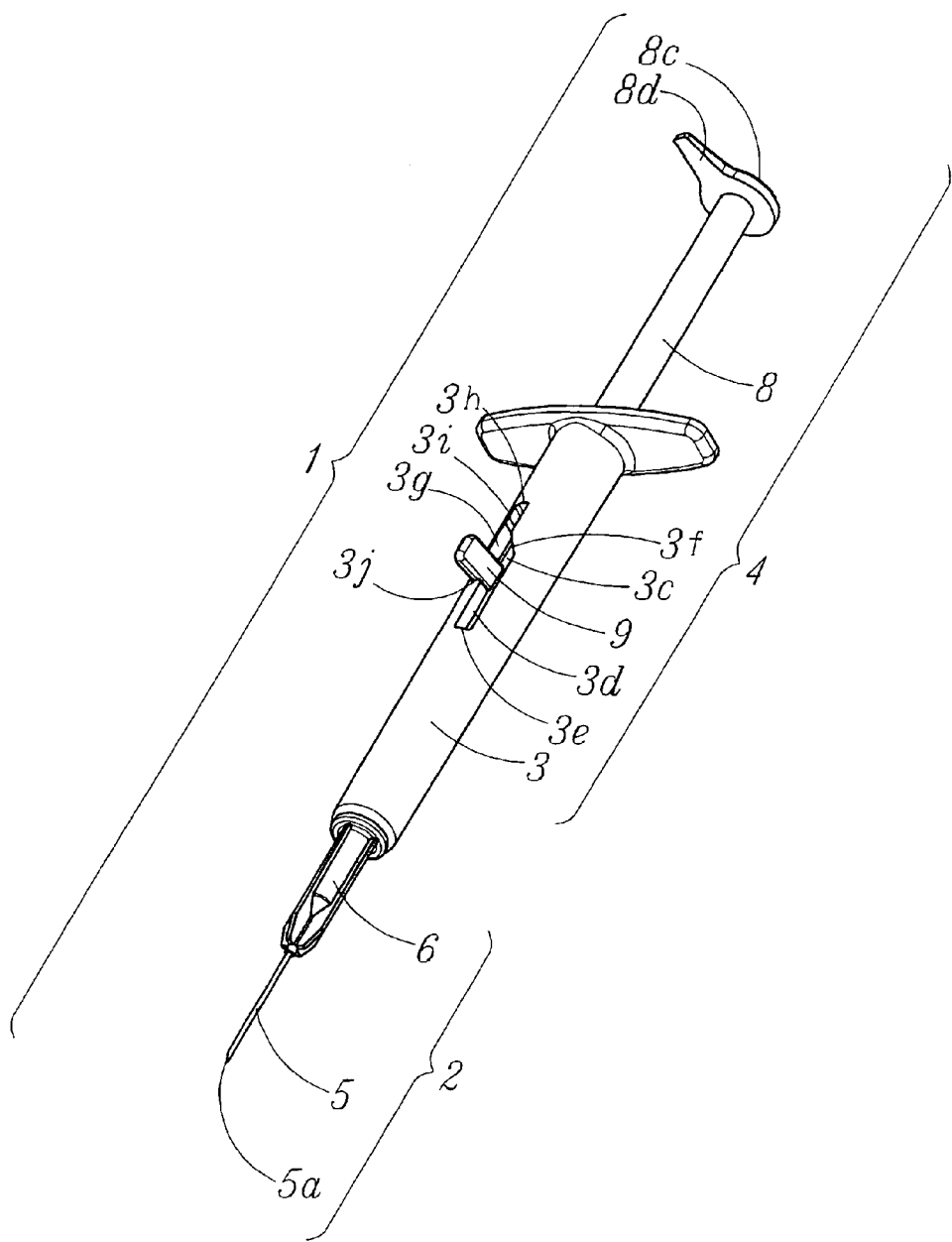
FIG. 5 is a perspective view of the entire syringe that is shown in FIG. 1 and acquired after completion of bubble removal shown in FIG. 1.
Figure 6:
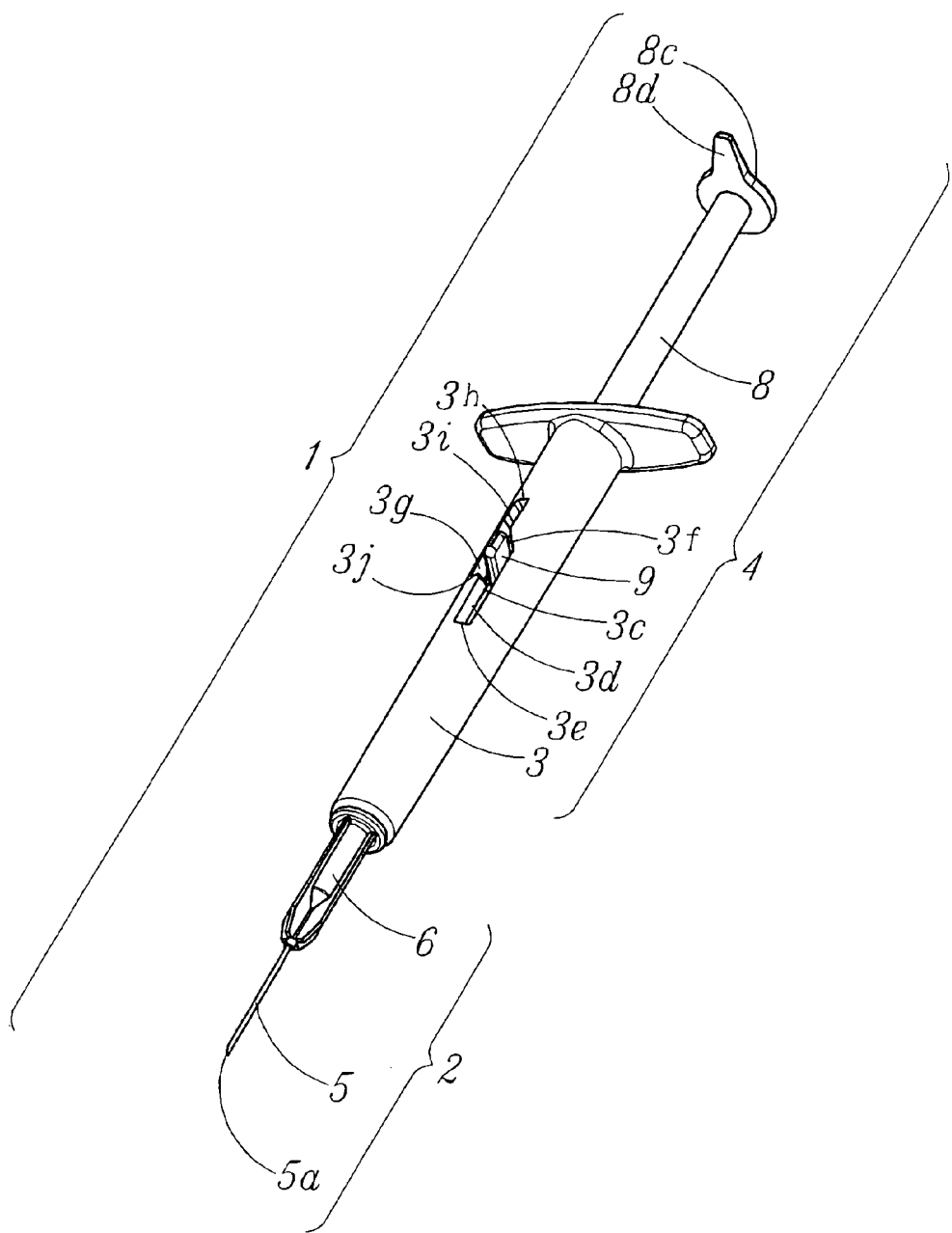
FIG. 6 is a perspective view of the entire syringe that is shown in FIG. 1 and acquired before dispensing.

Subsequently, operation for removing a bubble from the medical solution in the fluid chamber is performed. A rear end face 8c of the piston 8 is pushed to thereby move the piston set 4 toward the front, whereupon the slider 9 moves forwardly, decreasing the amount of the fluid chamber. Thus, the medical solution is ejected from a tip end hole 5a of the needle 5. When the piston set 4 is additionally kept moving toward the front, the slider 9 contacts a step (a target position contact portion) 3j of the guide 3c as illustrated in FIG. 5, so that the piston set 4 cannot advance any further. Removal of a bubble in the fluid chamber is completed in this state, and the fluid chamber defined between the syringe barrel 3 and the interior of the injection needle set 2 becomes free of air.

Dispensing operation is now performed. First, a projection 8d of the piston 8 is turned in a circumferential direction of the syringe barrel 3. The piston 8 is thereby turned, whereupon the slider 9 moves from the second groove 3g to the first groove 3d, so that the piston set 4 becomes able to move along a longitudinal direction. When the rear end face 8c of the piston 8 is further pushed, the slider 9 advances along the first groove 3d, whereupon the slider 9 contacts the front end face 3e of the first groove 3d as illustrated in FIG. 1. The piston set 4 is thereby situated at the foremost end, whereupon dispensing is completed. Thus, the syringe 1 enters the same state as that achieved before use of it.

Incidentally, the step 3j is placed at a location where the slider 9 contacts the step 3j when the amount of the fluid chamber becomes equal to a target amount which is a amount required for dispensing. To be specific, when the piston set 4 is moved forwards such that the slider 9 moves from the step 3j to the front end face 3e, the target amount of medical solution is ejected.

As above, in the syringe 1 of the embodiment, the step 3j is placed at the location where the slider 9 contacts the step when the amount of the fluid chamber becomes equal to the target amount which is the amount required for dispensing. For this reason, so long as the user pushes the rear end face 8c of the piston 8 until the slider 9 contacts the step 3j, the amount of medical solution in the fluid chamber can be set to a target amount. During this operation, since the user does not need to pay attention by particularly viewing the scale, or the like, the amount of the fluid chamber can be set to a target amount by simple operation. In addition, the operation does not require proficiency. Whoever the user is, he/she can set the amount of the fluid chamber to a target amount at all times by handling the syringe 1.

In the syringe 1 of the embodiment, a distance between the rear end face 3h and the step 3j of the guide 3c remains constant at all times. Specifically, since a range in which the slider 9 moves from a location where suction of the solution is completed to a location where removal of a bubble is completed is constant, the amount of medical solution ejected during operation for removing a bubble is also constant all of the time. Consequently, the medical solution can constantly used in an appropriate amount by appropriately setting distance between the rear end face 3h and the step 3j. An excessive amount of medical solution has hitherto been disposed in order to assure removal of a bubble, and the medical solution has been wasted. The syringe 1 of the embodiment, however, prevents wasteful use of a medical solution.

Although the invention has been described thus far by use of its embodiment, a technical scope of the invention is not restricted to the scope defined by the embodiment. It is manifest to those who are versed in the art that the embodiment be susceptible to a variety of alterations or modifications.

For instance, in the first embodiment, the method for fixing the injection needle set 2 is screw-engagement, and the end of the tube of the syringe barrel 3 has a thread shape. However, the injection needle set 2 can also be fixed by means of a Lure syringe method (i.e., a plug-in method) as in the case of a common syringe. In addition, the syringe barrel 3 can also be formed from a resin material, like PP (polypropylene), PE (polyethylene), and PET (polyethylene terephthalate) or a hard material made of stainless steel or glass.

In addition, although the slider 9 has a rectangular shape in the embodiment, the slider is not limited to the shape. The slider 9 can also assume; for instance, a square shape, a circular shape, an oval shape, or a gourd shape. Thus, the shape of the slider 9 is selectable as necessary.

Furthermore, the syringe barrel 3, the needle base 6, and the piston 8 are molded from a transparent resin, and the gasket 7 and the slider 9 are molded from an opaque, color resin in the embodiment. However, the syringe barrel 3, the needle base 6, and the piston 8 can also be molded from the opaque, color resin, and the gasket 7 and the slider 9 can also be molded from the transparent resin. Moreover, opaque resins or transparent resins can also be used for both, or semi-transparent resins can be used. Further, combinations of them are also selectable as required.

Although the syringe barrel 3, the needle base 6, the piston 8, and the slider 9 employ as a material a PP (polypropylene) resin in the preceding embodiment, a PE (polyethylene), or the like, can also be used. Moreover, although the gasket 7 uses butyl rubber, butadiene rubber, silicone rubber, an elastomer resin can also be used. Thus, the material of the gasket 7 can be selected appropriately depending on a situation where the gasket is to be used.

Figure 7:
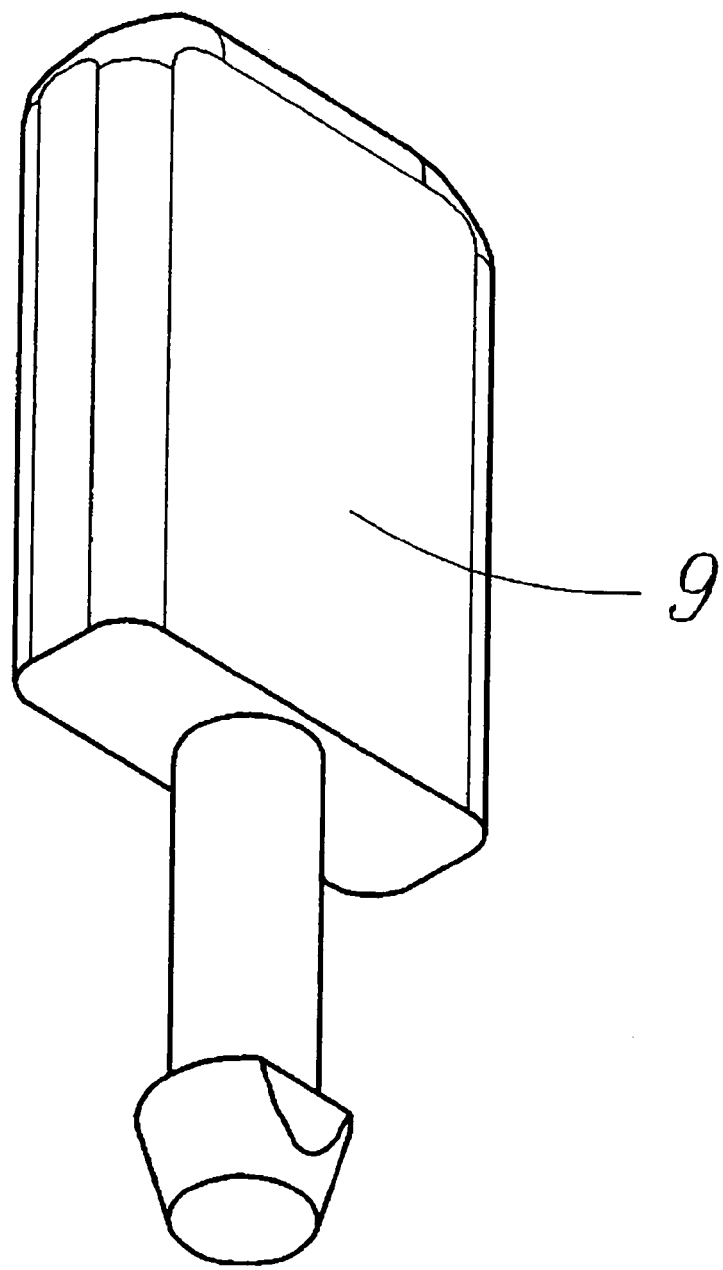
FIG. 7 is a perspective view of a modification of a slider.
Figure 8:
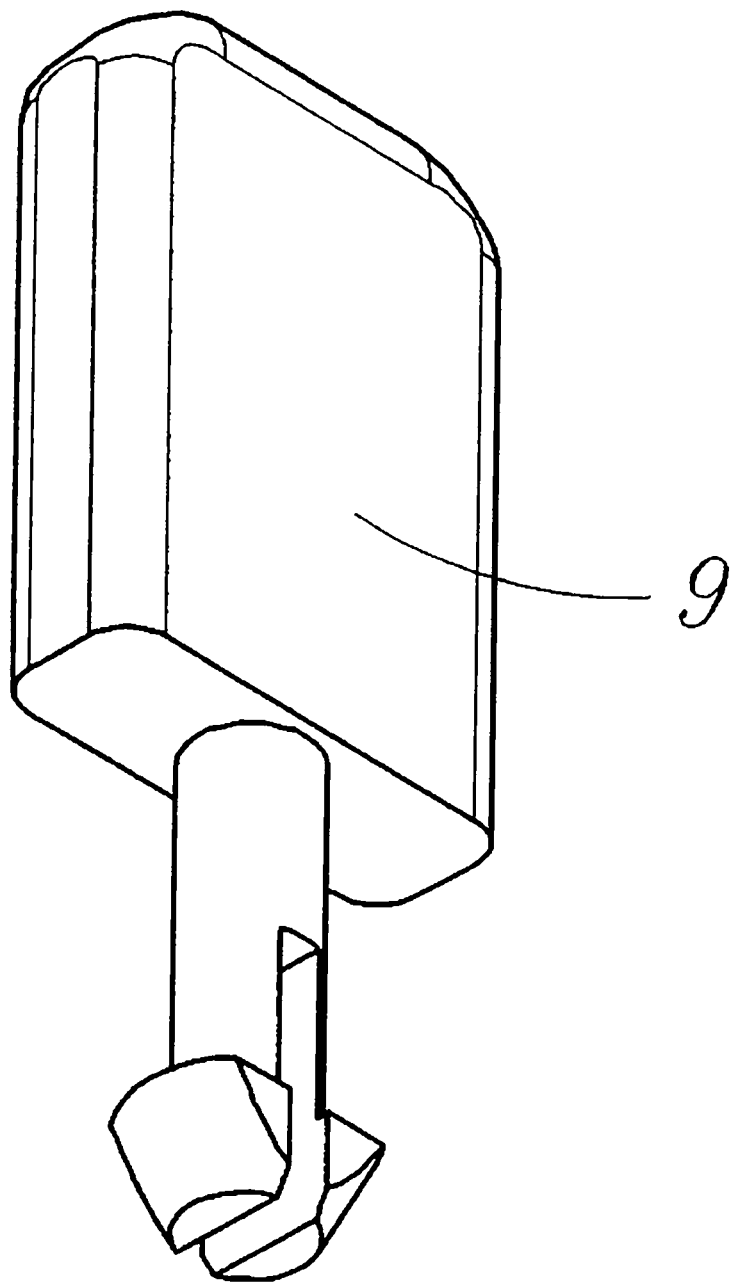
FIG. 8 is a perspective view of another modification of the slider.
Figure 9:
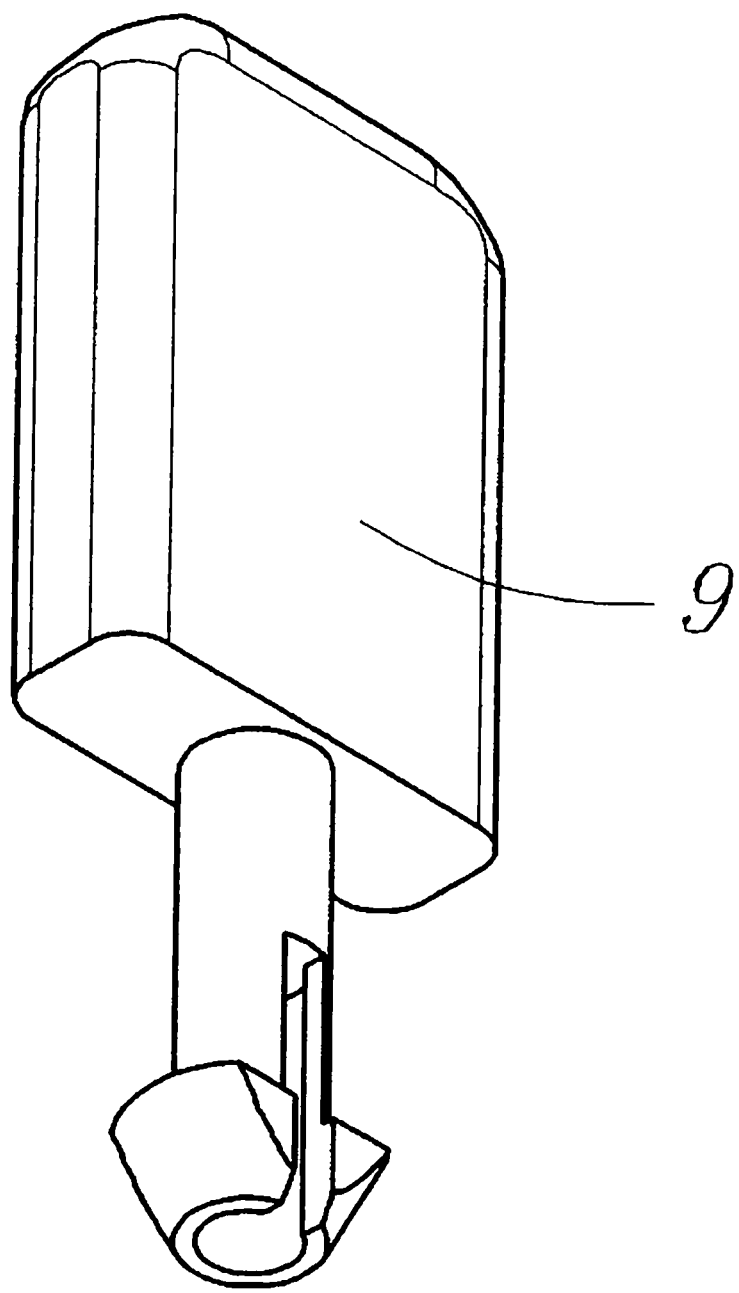
FIG. 9 is a perspective view of still another modification of the slider.
Figure 10:
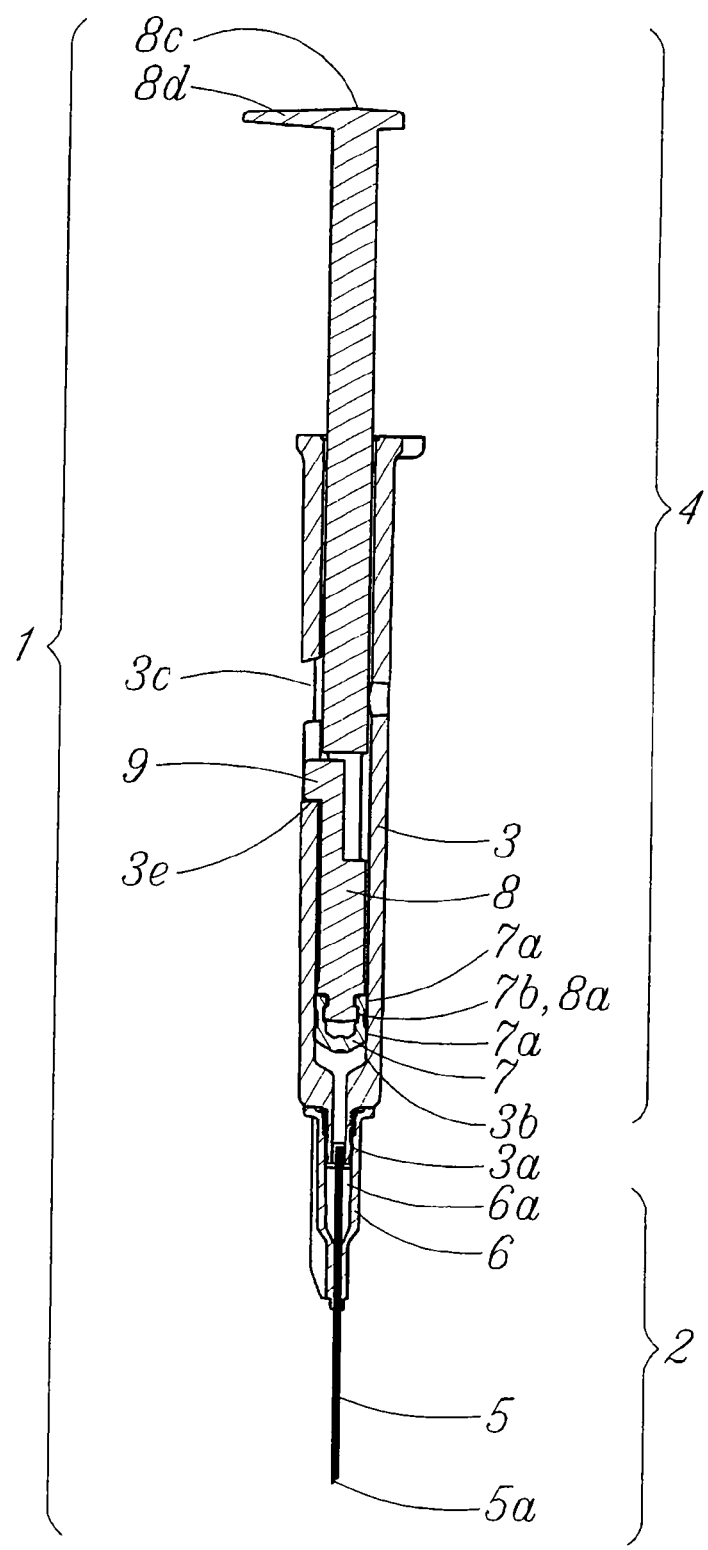
FIG. 10 is a cutaway side view of the syringe of the modification.

Various modifications of the shape of the slider 9 are now mentioned by reference to FIG. 7 to FIG. 10. In the embodiment, the slider 9 has a shape so that the slider 9 is press-fitted to the piston 8 so as not to get out of the piston 8. However, the shape of the slider 9 is not limited to this shape. The slider 9 can also has another shape; for instance, an arrow shape with a rotation stop as shown in FIG. 7; a shape including an arrow shape with a rotation stop and a slit, as shown in FIG. 8; a shape that is a combination of an arrow shape with a rotation stop and a C-shaped ring as shown in FIG. 9; and a shape in which the slider 9 is integrated with the piston 8 as shown in FIG. 10.

Features of the respective shapes are as follows. The arrow shape with a rotation stop shown in FIG. 7 is configured to prevent the slider 9 from getting out of the piston 8 by the arrow shape thereof. The shape shown in FIG. 8 that includes the arrow shape with a rotation stop and the slit is embodied by adding a slit to the shape shown in FIG. 7. By means of the slit, a tip end of the slider 9 becomes deformed during assembly of the syringe 1, thereby facilitating insertion of the piston 8 into the insert hole 8b.

Likewise, even in the shape shown in FIG. 9 that is a combination of the arrow shape with a rotation stop and the C-shaped ring, the tip end of the slider 9 becomes deformed during assembly by means of the C-shaped ring, thereby facilitating insertion of the piston 8 into the insert hole 8b.

The shape shown in FIG. 10 that integrates the slider 9 and the piston 8 together corresponds to a single component into which the slider 9 and the piston 8 are integrated. A notch is formed on the back of a projecting portion around an outer periphery of the slider 9, and the slider 9 is made elastically deformable within a space defined by the notch. When the piston set 4 is inserted from the back of the syringe barrel 3, the piston set 4 is inserted while the slider 9 of the piston 8 becomes elastically deformed, so that assembly is facilitated.

Moreover, explanations are given to the embodiment by taking the example in which the guide 3c includes the first groove 3d and the second groove 3g. However, the guide 3c can also be given multiple steps, such as three steps and four steps. In addition, the shape of the guide 3c can also be a circular arc shape or a spline curve rather than a linear shape. The shape of the guide 3c is now specifically described by reference to FIG. 11.

Figure 11:
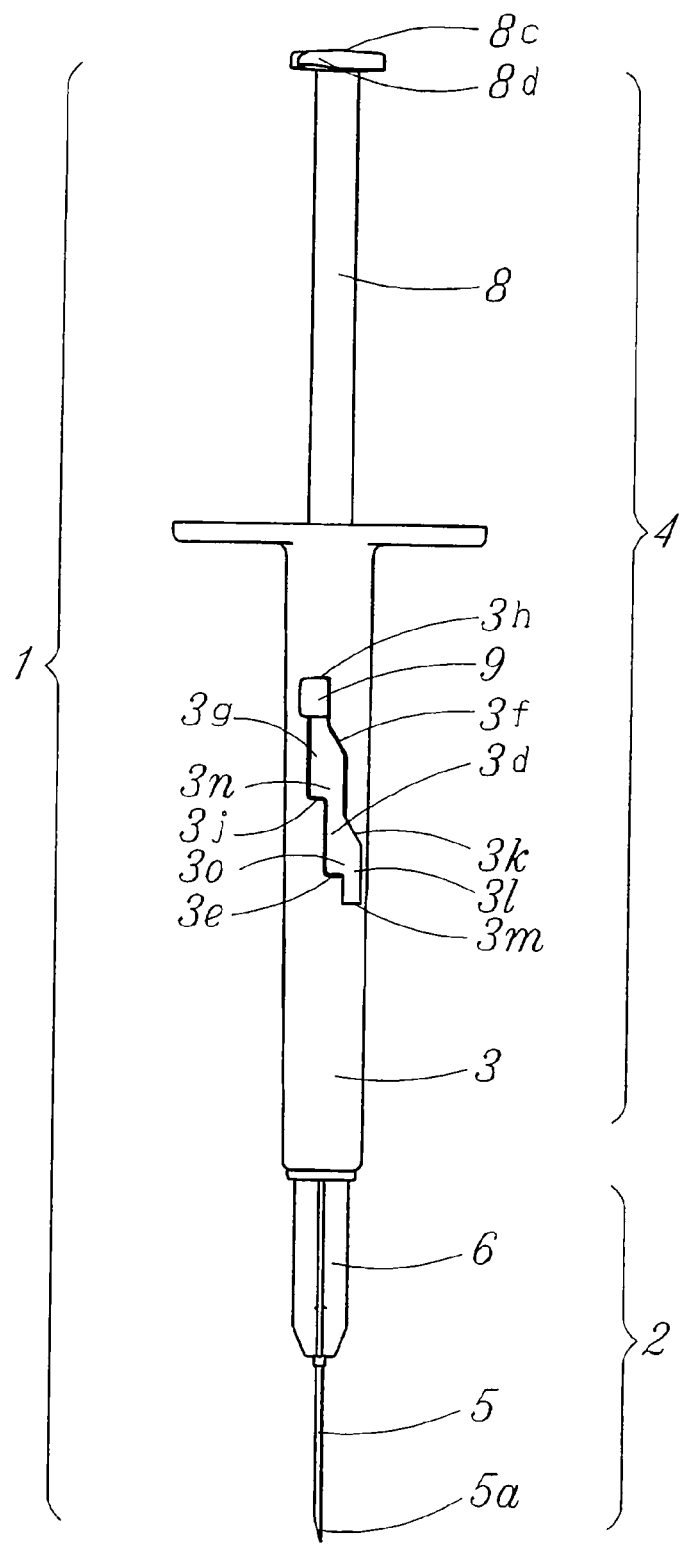
FIG. 11 is a front view of the syringe of the other modification.

FIG. 11 is a front view of the syringe 1 of the modification of the invention. In the modification, the guide 3c has a first groove 3d, a second groove 3g, and a third groove 3l. The three grooves 3d, 3g, and 3l are formed such that adjacent grooves have respective different axial lines. A sloped surface 3k connects a rear end of third groove 3l with first groove 3d. In addition, the first groove 3d and the second groove 3g, which are adjacent to each other, are connected at a first connecting portion 3n, and the first groove 3d and the third groove 3l, which are adjacent to each other, are connected at a second connecting portion 3o.

The first connecting portion 3n and the second connecting portion 3o are formed as spaces that extend along the peripheral direction of the syringe barrel 3. Further, portions of the wall that make up the first connecting portion 3n and the second connecting portion 3o are formed as the first step 3j and a second step 3e.

The first step 3j is placed at a location where the slider 9 contacts the step 3j when the amount of the fluid chamber becomes equal to the first target amount during movement of the slider 9 through an interior of the second groove 3g. The second step 3e is placed at a location where the slider 9 contacts the step 3e when the amount of the fluid chamber becomes equal to the second target amount during movement of the slider 9 through an interior of the first groove 3d. Further, a front end face 3m is placed at a location where the slider 9 contacts the front end face when the amount of the fluid chamber becomes equal to the third target amount during movement of the slider 9 through an interior of the third groove 3l.

The piston 8 is moved such that the slider 9 moves from the rear end face 3h through the interior of the second groove 3g until the slider contacts the first step 3j, whereby the medical solution can thereby be ejected in the first target amount. Furthermore, when the piston 8 is turned and moved in the longitudinal direction such that the slider 9 moves from the first step 3j through the interior of the first groove 3d in the circumferential direction, the medical solution can be ejected in the second target amount. Likewise, the piston 8 is moved such that the slider 9 moves from the second step 3e through the interior of the third groove 3l in the circumferential direction, whereby the medical solution can be ejected in the third target amount.

In the syringe 1 of the modification, when the slider 9 is moved through the interior of each of the first groove 3d, the second groove 3g, and the third groove 3l, the piston 8 is moved in the longitudinal direction. In the meantime, when the slider 9 is moved from the second groove 3g to the first groove 3d, the piston 8 must be turned along the circumferential direction in order to let the slider 9 pass through the first connecting portion 3n. As above, in order to let the slider 9 move from the second groove 3g to the first groove 3d, the direction of movement of the piston 8 must be changed. By the above configuration, since the slider 9 from continually moves from the second groove 3g to the first groove 3d, the first target amount of medical solution and the second target amount of medical solution can be ejected while distinguished from each other with certainty.

Such a configuration enables accurate ejection of a predetermined amount of medical solution in each of the steps during multi-step ejection operation. The respective steps can be separately used for specific targets. For instance, the first target amount can be used for infants; a total amount consisting of the first target amount and the second target amount can be used for children at and under the age of 12; and a total amount consisting of the first target amount, the second target amount, and the third target amount can be used for adults. One syringe 1 can thereby administer an accurate amount of medicine to a person no matter how old the person is or no matter what physique the person has. Further, the first target amount, the second target amount, and the third target amount can be set to an equal amount or to different amounts, respectively.

The respective grooves 3d, 3g, and 3l of the guide 3c can have a circular arc shape or a spline curve rather than a linear shape. When a person pushes an object, pushing action is performed while using many articulations, like fingers and a wrist of the person. For these reasons, the locus of pushing action is not straight, and pushing is performed while being slightly curved. The shape of the guide 3c is a circular shape or a spline curve in alignment with the locus of the human action, whereby operability of the syringe 1 is enhanced.

Moreover, the embodiment has been described by taking as an example the slider 9 that projects outside the syringe barrel 3. However, the slider 9 can also be accommodated within the syringe barrel 3. In this case, there is adopted a structure in which the piston 8 is provided with a guide; in which a projection that projects toward the piston 8 is provided on an inner diameter portion of the syringe barrel 3; and in which the guide on the piston is caused to fit into the projection. By means of the structure, the slider will not appear outside, so that the appearance of the syringe is improved.

Also, the embodiment has been described by taking an example in which the syringe barrel 3 is provided with the guide 3c and in which the slider 9 is attached to the piston 8. However, the invention is not limited to the embodiment. The syringe barrel 3 can also be provided with a slider, and the piston 8 can also be provided with a guide.

Figure 12:
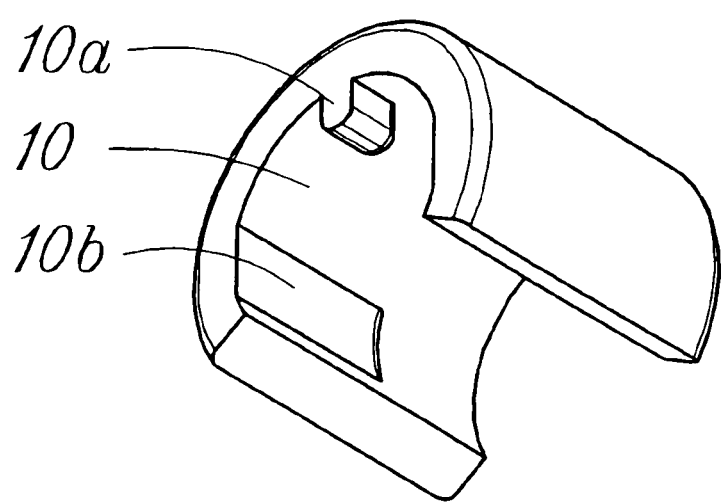
FIG. 12 is a perspective view of an adaptor to be attached to the syringe.
Figure 13:
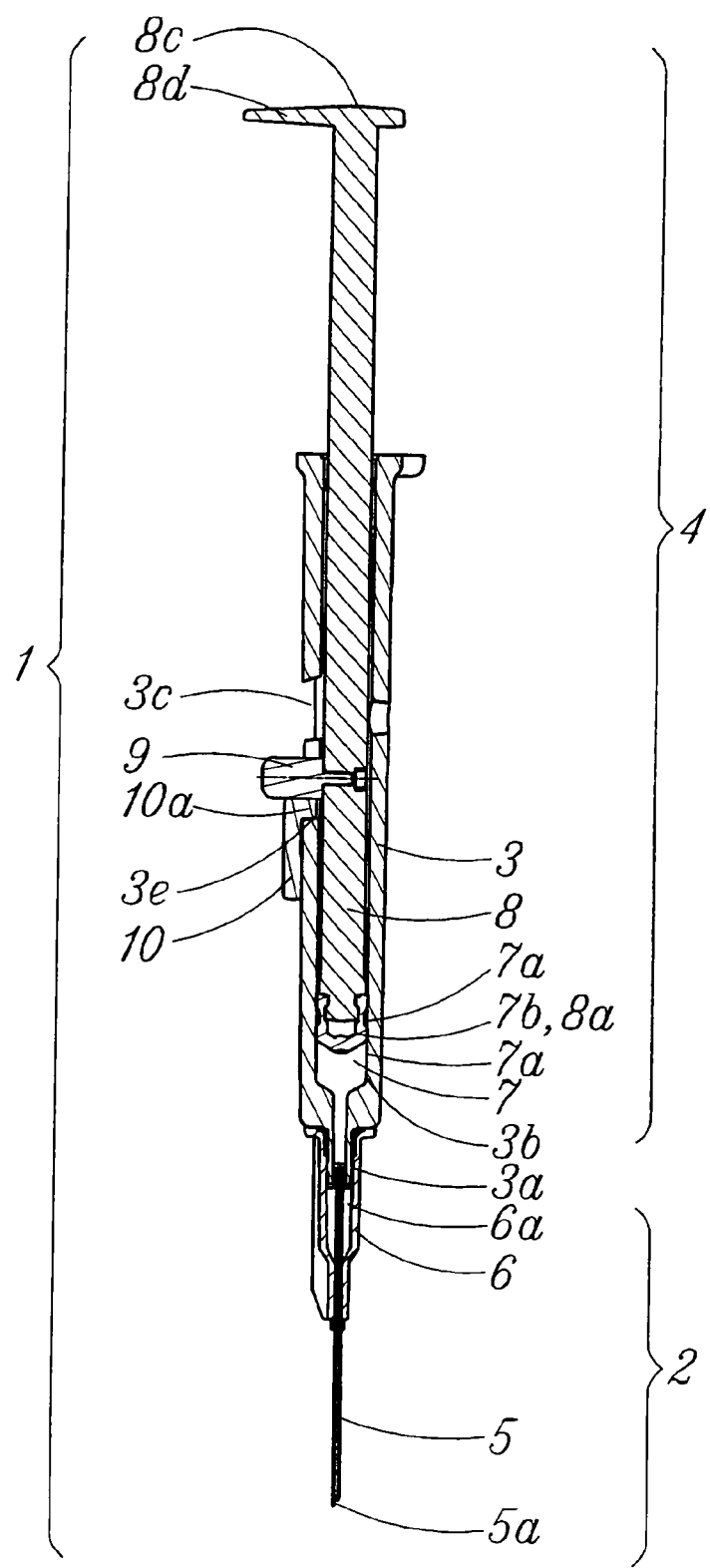
FIG. 13 is a cutaway side view of the syringe outfitted with the adaptor shown in FIG. 12.

An adaptor 10 that can be used while attached to the syringe 1 and is configured to change an ejection amount is now described by reference to FIG. 12 and FIG. 13. FIG. 12 is a perspective view of an adaptor to be attached to a syringe. FIG. 13 is a cutaway side cross sectional view of the syringe outfitted with the adaptor shown in FIG. 12.

The adaptor 10 is a member to be removably attached to a periphery of the syringe barrel 3. The projection 10a provided on an inner periphery of the adaptor 10 fits into the first groove 3d of the syringe barrel 3, thereby contacting the front end face 3e. Ribs 10b are provided on the inner periphery of the adaptor 10. As a result of the syringe barrel 3 being caught by the ribs 10b, the adaptor 10 is stationarily fixed while being lightly press-fitted to the outer periphery of the syringe barrel 3.

The projection 10a of the adaptor 10 prevents any further advancement of the slider 9 at a position in front of the front end face 3e. By means of a simple technique that allows attachment of the adaptor 11, the target amount can thereby be set to a smaller value. Further, the target amount can readily changed by changing the size of the adaptor 10.

The adaptor and the syringe are screw-engaged together and made movable in the longitudinal direction thereof, whereby the adaptor can be fixed at an arbitrary position. Thus, a container capable of ejecting a predetermined amount of various solutions is obtained.

In the embodiment, the invention has been described by taking as an example a syringe with an injection needle. However, the invention is not limited to the embodiment. The fixed amount discharge container of the invention is a container that can draw in and eject a predetermined target amount of solution. Hence, the fixed amount discharge container can be used as a container for administering a medicinal drink for infants, a container that draws in, by suction, and ejects a cosmetic aroma oil, a container utilized for refilling a vial with perfume water or personally blending perfume waters, or a container used for nursing a small animal or providing water to the small animal.

In addition, so long as the guide is given multiple steps, such as three steps and four steps, the syringe becomes useful in a case where a change is made to conditions for experiment of falling a predetermined amount of test reagent on a Petri dish, such as falling one milliliter of test reagent up to a second step and two milliliters of test reagent up to a third step.

The guide 3c is formed as a through hole that penetrates through the syringe barrel 3 in its radial direction; the shape of the slider 9 is set as illustrated in FIG. 7 to FIG. 10; and the slider 9 is removably attached to the piston 8. Assembly of the fixed amount discharge container thereby becomes facilitated. Furthermore, since disassembly of the fixed amount discharge container is also easy, the fixed amount discharge container can be recycled by disassembling the dispenser, cleansing parts, and reassembling the parts.

Although the invention has been specifically described with reference to the specific illustrative embodiments, it is apparent to one skilled in the art that a variety of changes and modifications can be made without departing from the spirit and scope of the invention.

This application is based on Japanese Patent Application No. 2011-098003 filed on Apr. 25, 2011, the disclosures of which are incorporated herein by way of reference.

INDUSTRIAL APPLICABILITY

The fixed amount discharge container of the invention allows the user to ascertain a point in time when a amount of a fluid chamber filled with fluid becomes equal to a target amount from the fact that a slider has contacted a target position contact portion. Accordingly, the invention can provide a fixed amount discharge container that can readily, accurately eject fluid in a target amount at all times.

The invention claimed is:
1. A fixed amount discharge container comprising:
a syringe barrel; and a piston, inserted in the syringe barrel so as to be movable in a longitudinal direction, thereby defining a fluid chamber between the syringe barrel and the piston, wherein one of the syringe barrel and the piston includes a guide that is extended in the longitudinal direction, the guide including a plurality of grooves, each groove having a first side and a second side, the first and second sides extending axially with respect to the one of the syringe barrel and the piston, the first side extending forwardly to a front end face of the each groove, the front end face extending from a front end of the first side of the each groove circumferentially with respect to the one of the syringe barrel and the piston toward the second side of the each groove to a rear end of a first side of an adjacent groove, and adjacent grooves connected to one another by a sloped surface extending from a forward end of a second side of one of the grooves forwardly and away from the first side of the one of the grooves to a rear end of a groove adjacent to the one of the grooves;

the other of the syringe barrel and the piston includes a slider that is movable in the guide along with the other of the syringe barrel and the piston, and the guide is provided with a target position contact portion which the slider contacts when an amount of the fluid chamber is equal to a target amount.

2. The fixed amount discharge container as set forth in claim 1, wherein the grooves that are adjacent to each other are formed such that axial lines of the grooves differ from each other;

the grooves that are adjacent to each other are connected at a connecting portion; and one of the front end faces is the target position contact portion.

3. The fixed amount discharge container as set forth in claim 1, wherein the guide is formed in the syringe barrel as a through hole that penetrates through the syringe barrel in a radial direction; and the slider is removably attached to the piston from the outside the syringe barrel.

4. The fixed amount discharge container as set forth in claim 1, further comprising an adaptor that changes the target amount.

5. The fixed amount discharge container as set forth in claim 2, wherein the slider moves to one of the grooves along the sloped surface.

* * * * *